(12) United States Patent
Cros et al.

(10) Patent No.: US 9,597,233 B2
(45) Date of Patent: Mar. 21, 2017

(54) ADAPTED COMPRESSION/SPLINT ORTHOSIS FOR REINFORCEMENT OF THE CALF MUSCULOANONEUROTIC PUMP

(71) Applicant: Innothera Topic International, Briand, Arcueil (FR)

(72) Inventors: Francois Cros, Ivry sur Seine (FR); Gregory Thiney, Asnieres sur Seine (FR)

(73) Assignee: Innothera Topic International, Arcueil (FR)

( * ) Notice: Subject to any disclaimer, the term of this patent is extended or adjusted under 35 U.S.C. 154(b) by 0 days.

(21) Appl. No.: 15/055,782

(22) Filed: Feb. 29, 2016

(65) Prior Publication Data

US 2016/0175159 A1    Jun. 23, 2016

Related U.S. Application Data

(63) Continuation of application No. 13/683,371, filed on Nov. 21, 2012, now Pat. No. 9,308,116.

(51) Int. Cl.
| | | |
|---|---|---|
| *A61F 13/00* | (2006.01) | |
| *A61F 5/40* | (2006.01) | |
| *A61F 13/08* | (2006.01) | |
| *D04B 1/26* | (2006.01) | |

(52) U.S. Cl.
CPC .......... *A61F 13/00987* (2013.01); *A61F 5/40* (2013.01); *A61F 13/08* (2013.01); *D04B 1/265* (2013.01); *A61F 2013/00574* (2013.01); *A61F 2013/00625* (2013.01); *A61F 2013/00629* (2013.01)

(58) Field of Classification Search
CPC ...... A61F 13/08; A61F 13/0273; A61F 13/00; A61F 5/40; D04B 11/28; D04B 1/06; A41B 11/00
See application file for complete search history.

(56) References Cited

U.S. PATENT DOCUMENTS

| | | |
|---|---|---|
| 2,901,901 A | 9/1959 | Baker |
| 4,008,350 A | 2/1977 | Crawford et al. |
| 5,258,036 A | 11/1993 | Edenbaum et al. |
| 2009/0240279 A1 | 9/2009 | Becker |

FOREIGN PATENT DOCUMENTS

| | | |
|---|---|---|
| EP | 0934043 | 7/2001 |
| EP | 1240880 | 9/2002 |
| EP | 1656916 | 5/2006 |
| FR | 2606629 | 5/1988 |

(Continued)

*Primary Examiner* — Ophelia A Hawthorne
(74) *Attorney, Agent, or Firm* — Jacobson Holman PLLC

(57) ABSTRACT

An orthosis (10) has an elastic compressive distal portion (14), extending upwards from the ankle, associated with an adjacent rigid splint proximal portion (16), enveloping the region of the calf between the level of the point where the Achilles tendon joins the calf muscles and the level located below the tibial tuberosity. This rigid splint proximal portion (16) is an essentially non-elastic, deformable tubular portion, made by: placing the orthosis onto a template representative of the morphology of the patient's calf; applying in situ on the orthosis, in the region of the splint proximal portion, a hardenable biocompatible resin; hardening the resin with the orthosis maintained on the template; and removing the orthosis in its finished state.

12 Claims, 1 Drawing Sheet

(56) References Cited

FOREIGN PATENT DOCUMENTS

| | | |
|---|---|---|
| FR | 2824471 | 11/2002 |
| FR | 2912644 | 8/2008 |
| WO | WO 2006/134875 | 12/2006 |
| WO | WO 2011/023650 | 3/2011 |
| WO | WO 2011/143489 | 11/2011 |

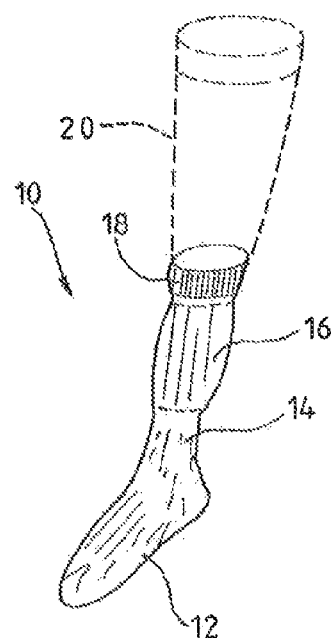
FIG._1
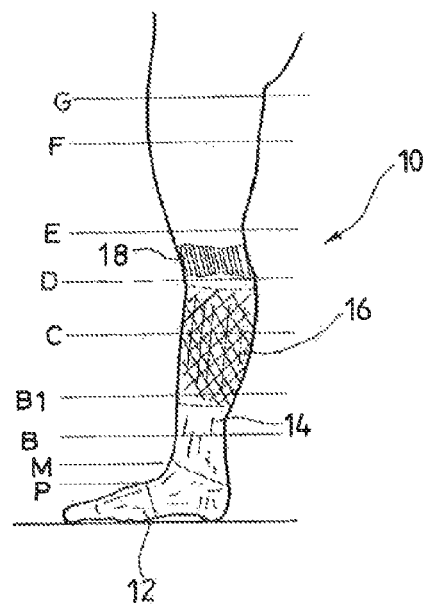
FIG._2
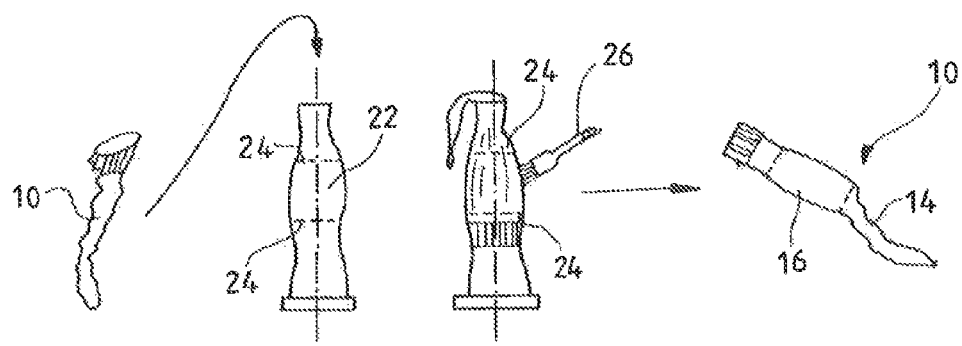
FIG._3

ADAPTED COMPRESSION/SPLINT ORTHOSIS FOR REINFORCEMENT OF THE CALF MUSCULOANONEUROTIC PUMP

The invention relates to the elastic venous compression (EVC) orthoses, indicated in the various clinical manifestations of venous insufficiency of the lower limbs.

Such orthoses, formerly known as "elasticated stockings (or socks)" or "elasticated tights", are textile medical devices that produce a therapeutic effect by compression of the lower limbs, in contrast to the "sustain stockings" (also "support stockings" or "anti-fatigue stockings") and to the "fashion stockings", which are not medical devices with a therapeutic purpose.

EVC orthoses are designed to produce a therapeutic effect by compression of the lower limb over a greater or lesser extent, usually with an upwardly degressive profile starting from the ankle. Depending on the type of orthosis, the pressure measured at the ankle may vary from 10 to more than 36 mmHg (i.e. from 13 to 48 hPa, the unit mmHg being however commonly used as a pressure measurement unit in the field of phlebology and medical compression). In France, stockings are divided into four textile classes according to the ASQUAL system, namely Class I (13 to 20 hPa≈10 to 15 mmHg at the ankle), class II (20 to 27 hPa≈15 to 20 mmHg), class III (27 to 48 hPa≈20 to 36 mmHg), and class IV (>48 hPa≈>36 mmHg). These compression classes may be different in other countries.

For a high compression of the lower limbs, such orthoses are made from a knit fabric of more or less tight texture with incorporation of an elastic weft yarn, generally a covered spandex yarn.

More precisely, under the effect of being placed on the limb, the tight textile of the orthosis exerts a compression resulting from the return force of the elastic fibers that make up the material, and the application of such elastic return forces on the perimeter of the outline generates at a given point, according to the Laplace law, a local pressure that is inversely proportional to the radius of curvature of the outline at that point.

This pressure is the "textile pressure" as defined and calculated within the meaning of the French standard NF G 30-102, part B. The term "pressure" will be used hereinafter to refer to the mean of the pressures locally exerted at a given altitude along an outline of the leg.

The knit and the yarns, as well as the dimensioning of the rows of stitches, are selected so that predetermined pressures are applied at different altitudes along the lower limb, e.g. at the height of the ankle, at the start of the calf, at the calf, at the popliteal fossa, etc., all the way up to the top of the thigh, such altitudes being conventionally denoted B, C, . . . , G. These various pressures are defined for each class with reference to metrological templates such as the model leg of the French standard NF G 30-102 part B, Appendix B, corresponding to the "Hohenstein" model leg according to the German system RAL-GZ 387, or as defined in the European Pre-Standard XP ENV 12718; 2001.

The above-mentioned characteristic of pressure profile degressivity consists in exerting a maximum pressure at the ankle, then a degressive pressure from the ankle to the calf or to the thigh. It is based on the fact that, in an orthostatic situation, the intravenous pressure is degressive from the ankle to the calf, then up to the thigh. It is therefore logical to apply a corresponding, and hence degressive, counter-pressure, to proportionally reduce the venous diameters and to induce an anti-stasis effect.

In a dynamic situation, such as during walking, the situation is physiologically different, the calf being the key element of the lower limb venous hemodynamics.

The importance of the effect of the "muscle pump" or "calf musculo-aponeurotic pump" (CMAP) has notably been described in terms of return venous blood flow, where the physiological cycles of contraction and relaxation of the calf muscles give rise, via the opening and closing actions of the venous valves, to emptying and filling of the lower limb venous network, which results in a lowering of the venous pressure at the ankle. The CHAP efficiency decreases progressively with the age of the subjects, which is accompanied by a residual venous hyper-pressure that naturally aggravates chronic venous insufficiencies.

Chronic venous insufficiency is therefore characterized by a failure of this muscle pump effect, which hence plays a major role in the genesis of the trophic troubles such as ulcers.

The starting point of the invention is the search for a means making it possible to improve the CMAP efficiency, or even to take over from it, thanks to a compressive orthosis that is better suited to this role than the orthoses that may have been proposed up to now and that are degressive, because they are based on the analysis of the venous pressures resulting from orthostatic situations.

However, the study of venous physiology, in particular using the recent compression modeling and simulating tools such as those described in the WO 2006/087442 A1 (Laboratoires Innothera), shows that the effectiveness of an EVC orthosis rather lies in the CMPA efficiency improvement, providing that it is possible to make it operate.

The FR 2 824 471 B1 (Rodier) describes an approach consisting in providing an "elective compression/splinting" by means of a differentiated-knit multizone stocking, associating a very elastic knit region at the foot and the ankle, followed by a not very elastic knit region from the bottom of the calf up to the popliteal fossa, and continued by again a very elastic knit region from the knee up to the top of the thigh. The basic idea consists in providing zones with a rather compressive effect (foot, ankle and thigh) on either side of a zone with a rather splinting effect (calf). This latter zone of the orthosis will produce less effect at rest than those that surround it. But, during contractions of the calf muscle, it will exert an increased compression, increasing the power and reinforcing the emptying effect of the CMAP.

In this respect, it should be specified that the terms "compression" and "splinting" define clearly different effects, even though they are sometimes confused in the common language:

"compression" is the effect produced by an elastic orthosis, both at rest and on effort, on a limb segment, as a result of the more or less strong return forces of the elastic fibers of this orthosis. These forces act in an almost constant manner on the limb: at rest, the compression is present at the nominal pressure value, and on effort, the effect of this compression is slightly increased by the contraction of the muscle masses;

conversely, "splinting" is the effect produced by an orthosis that acts in a differentiated manner (effort/rest) on a limb segment, under the action of a structure considered as being inelastic (but deformable), for example a non-elastic bandage, also referred to as "short-stretch bandage". At rest, this type of bandage exerts a low pressure, or even no pressure; on the other hand, during muscle contraction, it goes against the local volume increases of the calf, which comes into abutment with the non-elastic structure, the pressure being therefore strongly increased. The splinting is thus effective and active on effort, and almost inactive at rest.

It is customary in the scientific literature on this subject to consider that an orthosis is a splint, or "rigid", orthosis when it produces an increase of at least 10 mmHg (13 hPa) per centimeter of increase of the limb circumference at the point located where the Achilles tendon joins the calf muscles. The term "rigidity" is understood herein within the meaning of the definition of the European Pre-Standard XP ENV 12718:2001, i.e. "the increase of compression per centimeter of increase of leg circumference, expressed in hectopascais per centimeter and/or in millimeters of mercury per centimeter".

It is in order to denote these two different notions that the two respective terms "compression" (or "compressive") and "splinting" (or "splint") will be used herein-after.

With regard to these definitions, the proposal of the above-mentioned FR 2 824 471 B1, which implements only yarns and stitches that are more or less elastic over the height of the orthosis, produces only a very partial splinting effect at the calf.

Other orthoses consisted of zones, all of which are elastic but with a differentiated elasticity are proposed by the EP 0 934 043 B1 (Couzan) or EP 1 240 880 A2 (Stolk). These two documents teach the making of a stocking or a sock with a less rigid (more elastic) zone in the region of the calf, respectively uniformly over the whole circumference of the calf, or only in the posterior region thereof. The orthoses described, which are devoid of any inelastic structure, thus provide no "splinting" effect, within the above-explained meaning, with an effect of abutment of the calf against a non-elastic structure, in case of local volume increase of the latter.

The same is true for the product disclosed in the WO 2006/134875 A1, which provides discrete elements added at selected locations of an "anti-fatigue" sock or stocking, and intended to increase the sensation of compression felt by the wearer, hence without any splinting purpose or function. Moreover, none of these elements extends over the circumference of the calf, and therefore none of them can generate a splinting, since they cannot create an inelastic obstacle to the volume increase of the calf on effort.

In addition, from the technological point of view, in practice, it proves to be difficult to make all of those prior art "multizone" structures, taking into account the difficulty that exists in setting the knitting machine to obtain the required variable elasticity profiles, with very abrupt transitions between very heterogeneous textures that correspond to the different zones of the stocking or the sock.

On the other hand, and above all, those orthoses that may be referred to as "semi-splint orthoses" are not specifically fitted to a given patient. In concrete terms, the practitioner just selects an orthosis from a grid of sizes after having measured the perimeter of the ankle and of the calf. In practice, this leads to a compromise solution that does not take into account the real morphology of the calf, which may vary widely from one patient to another and which cannot be suitably described by merely measuring the maximum perimeter of the calf.

This drawback is particularly increased within the framework of products that are supposed to produce a real splinting effect (within the above-defined meaning), since the reinforcement of the CMAP effect depends on a precise fitting of the non-elastic structure to the concerned limb segment, over the whole extent thereof: if the non-elastic structure is not in close contact with the limb at rest, it will produce only very little effect for a small or moderate volume increase of the muscle; on the contrary, if its size is too small, it will exert stress on the limb even at rest, with harmful effects on blood circulation, in addition to an oppressive sensation that could make the orthosis particularly uncomfortable to wear for the patient.

It thus appears desirable that orthoses can be made, which provide a real splinting effect on the calf via a non-elastic structure (and not a structure with a lesser elasticity), fitted to the exact morphology of the limb segment of each patient.

The non-elastic structure must however be deformable, unlike for example the product disclosed by the EP 1 656 916 A1, which is a non-deformable orthopedic splint orthosis, intended to form a splint for immobilizing a traumatized limb: the splinting is not of same nature than that of the present invention, which must be implementable by an item, such as a stocking or a sock, liable to be put on and removed at will by the patient, and which, once in position, do not hinder the movements of the limb enveloped by the orthosis.

If it is desired to have a made-to-measure, rigid splint product, specifically fitted to the patient, a first solution consists in using multilayer bandages, with the well-known difficulty in properly adjusting the bandage, neither too tight (it would squeeze the calf) nor too loose (it would produce no effect), hence a highly "operator-dependent" result. As explained hereinabove, the adjustment of rigid splint product is highly critical, unlike a compressive elastic structure that is much more tolerant.

Moreover, the bandage needs to be regularly redone, each time with the same care for a good adjustment.

The FR 2 912 644 (Mollard et al.) discloses such a technique with, in addition, superimposition of a compressive element and a splint element. The splint element is a strip of perforated ultra-thin film, for example of polyethylene, packed as a roll. This film is unrolled around the limb in such a way to envelop the latter, then a splint stocking is placed on the bandage so at the provide the compressive effect. But, in addition to the particular skill required for placing the bandage, once the latter has been placed, no possibility exists to readjust it, except redoing the whole process. Finally, this product is single use and does not permit a temporary removal of the orthosis, for example for the time to make an examination or to change a dressing.

For those reasons, patients generally prefer using another solution, in the form of knitted orthoses to be slipped on, which are handier and more aesthetically pleasant.

The matter is then to make a made-to-measure, rigid product, perfectly fitted to the particular morphology of the patient. The technique consists in measuring the calf in the more complete way possible, with measurements at several heights. The orthosis is then knitted on a flat knitting machine, and shaped through a seam made all along its length, which requires an additional step of making. It will be understood that such a technique of full made-to-measure tailoring is lengthy to implement, complicated and thus expensive, and does not allow the rigid splint products to become widespread, despite their manifest therapeutic advantages.

The problem of the invention is thus to be capable of making a splint orthosis (a rigid product) able to be in the form of a final product that is "made-to-measure", hence perfectly fitted to the patient's morphology, but that do not even so require to be made using conventional, lengthy and expensive "made-to-measure" techniques.

In particular, it will be seen that the invention can be implemented i) on a circular knitting machine (and not a flat knitting machine, which would require an additional step of making for sewing the seam) ii) making a standard product, hence with a possibility to be made at a reasonable cost and in large quantities.

And this with a new EVC orthosis structure:
that reinforces the beneficial effects of the CMAP by an appropriate splinting of the calf;
that is technologically easy to make; and
that can be easily fitted to the very different leg morphologies encountered in the population of the concerned patients.

It will also be seen that the invention makes it possible to obtain an EVC orthosis for the lower limb that applies on the calf no longer a more or less strengthen compression, but a real splinting, by placing around the calf an essentially rigid, i.e. non-elastically deformable, element. In addition, with this high rigidity at the calf (splinting effect) will be associated a low rigidity at the ankle (compression effect).

Indeed, a high rigidity at the calf is considered as a means for optimizing the CMAP, which is the main motor of the venous return in the lower limbs. But the high rigidity at the calf has to be associated with a low rigidity (and hence a high deformability) at the ankle to ensure that the product will be easy to put on, to take off, and will be well tolerated—in particular to avoid a too high compression, which would rapidly become intolerable, in particular for a patient who is confined in bed or inactive.

A solution to that problem is described by the applicant in the EP 2 452 658 A1 (published on May 16, 2012, hence after the priority date of the present application). This solution consists in incorporating, during the making, a thermoformable yarn to the weft of the orthosis, in the region of the calf. The orthosis is then placed on a model and locally heated so as to become inextensible, and hence to form a splint, in this region, under the effect of changes of the thermoformable yarn mechanical characteristics.

However, this solution requires a modification of the knitting process so that the thermoformable yarn can be incorporated during the making of the orthosis.

The present invention aims to offer an alternative to this solution, which does not suffer from this drawback and which can be implemented based on an orthosis of conventional structure, without modification of the knitting process.

Essentially, the basic idea of the invention consists in making a compressive orthosis by means of conventional techniques, but with integrating into the product a splint portion made by applying and drying a suitable biocompatible resin, making it possible to obtain a hardening of the textile in the region where this resin has been applied.

If this operation is made with the orthosis placed on the patient's leg—or, preferably, on a template representative of the morphology of this leg, to avoid the patient the annoyance caused by the operation—and if the application of resin is properly located in the calf region, a compressive/splint product perfectly fitted to the shape of the patient's calf will finally be obtained.

Therefore, the product thus obtained makes it possible to apply an efficient splinting to the calf, thanks to the splint portion, whose shape will be personalized as a function of the patient, this region being in a way "molded in place" on the patient's calf. This splint portion in the calf region will be associated with a conventional compressive portion over the remainder of the leg, especially in the ankle region.

More precisely, the invention proposes an EVC orthosis having the same purpose as the above-mentioned FR 2 824 471 B1, i.e. a medical compression orthosis in the form of a sock, a stocking or a pair of tights intended to act specifically on the CMAP.

Such an orthosis comprises, in a manner known in itself, (i) an elastic compressive distal portion, adapted to cover the ankle, extending to before the beginning of the calf, at the point where the Achilles tendon joins the calf muscles, such point being generally denoted B1, and (ii) a splint proximal portion, continuing the compressive distal portion and adjacent thereto, and enveloping, over the circumference thereof, a region of the calf comprised between the level of the point where the Achilles tendon joins the calf muscles and the level located below the tibial tuberosity.

The distal portion is made by knitting a knit yarn and a weft yarn, the dimensioning and the nature of the knit and weft yarns as well as the knit structure being selected in such a way to exert in the circumference direction, once the orthosis has been placed on the limb, an elastic return force likely to produce a compression of the limb at a desired therapeutic level of pressure. The splint proximal portion is a deformable tubular portion that is knitted in continuation of the elastic compressive distal portion.

Characteristically of the invention, the splint proximal portion is essentially non-elastic, and incorporates a hardened biocompatible resin, for example an evaporation-hardenable single-component acrylic resin.

The knit yarn may in particular be a polyamide and/or cotton covered spandex yarn, and the weft yarn a polyamide and/or cotton covered spandex yarn.

The proximal portion may be a portion with, at the level of the calf maximum circumference, a high rigidity, of 15±2 mmHg/cm (≈20±2 hPa/cm), or a moderate rigidity, of 5±2 mmHg/cm (≈7±2 hPa/cm).

The elastic compressive distal portion may be a low compression portion adapted to exert a pressure of 10 to 20 mmHg (13 to 27 hPa), or a moderate compression portion adapted to exert a pressure of 20 to 30 mmHg (27 to 40 hPa) at the level of the ankle minimum circumference.

The invention also provides a specific method for tailoring an orthosis for medical compression/splinting of the lower limb to the measure of a patient's leg.

This method comprises the steps of: obtaining an orthosis as described above, in a rough initial state, with no biocompatible resin; placing the orthosis onto a template representative of the morphology of the patient's calf; applying in situ on the orthosis, in the region of the splint proximal portion, a hardenable biocompatible resin; hardening the resin with the orthosis maintained on the template; and removing the orthosis in its finished state. The orthosis has then a splint proximal portion made rigid following the hardening of the resin and keeping the corresponding dimensions of the patient's calf, which allows this splint proximal portion to perfectly fit the shape of the calf.

BRIEF DESCRIPTION OF THE DRAWINGS

An exemplary embodiment of the invention will now be described, with reference to the appended drawings, in which the same reference numbers designate identical or functionally similar elements throughout the figures.

FIG. 1 is an overall view of an orthosis according to the invention, in its free state.

FIG. 2 is an elevation view of the same orthosis, slipped on a limb, wherein the various standard altitudes to which are measured the pressures applied by the orthosis on the limb are indicated.

FIG. 3 illustrates the successive steps of the method of implementation according to the invention, intended to tailor the orthosis to the measure of the patient's leg.

In FIGS. 1 and 2, the reference 10 generally denotes the orthosis of the invention, which is a knitted orthosis made using conventional methods on a circular knitting machine. This tubular-shaped orthosis 10 comprises a portion 12 that envelops the foot and a portion of the leg, with a distal portion 14 enveloping the ankle and a proximal portion 16 enveloping the calf. The whole extends up to a level located below the knee, when the orthosis is a "knee-length" sock (or "calf-length sock"). In the latter case, the orthosis is terminated by a "ribbed type" knitted terminal portion 18.

This sock-shaped configuration is not limitative, and the invention may also be implemented as a "thigh-length" stocking, extended by a compressive thigh portion 20. The orthosis of the invention may also be made as a pair of tights, and/or be devoid of a foot portion 12 ("footless" type stocking or pair of tights).

The various adjoining portions of the above-described orthosis are knitted continuously on the circular knitting machine, i.e. making this orthosis does not require any step of making for assembling distinct parts, except naturally the operations for sewing the tip at the foot part 12, if a tip is present.

FIG. 2 shows the various altitudes of the lower limb as defined by the morphological system specified in the introduction (the "Hohenstein" model leg), using the standard notation:

B: ankle, at the point of its minimum circumference;
B1: point where the Achilles tendon joins the calf muscles;
C: calf, at the point of its maximum circumference;
D: just below the tibial tuberosity (i.e. just below the knee);
E: at the center of the kneecap and above the back of the knee (i.e. at the level of the popliteal fossa);
F: at the middle of the thigh; and
G: at the top of the thigh.

The calf is the limb segment comprised between the levels B1 and D, and the ankle is the limb segment located below the level B1.

The pressure exerted at the altitude B (at the minimum perimeter of the ankle) is the pressure prescribed for the selected standard class (I, II, III, or IV).

The pressure values may be read, for example, using a dynamometer according to the above-mentioned standard NF G 30-102 part B, after the orthosis has been slipped on a reference template such as the Hohenstein model leg prescribed by that standard.

The pressure exerted on the ankle at the point of its minimum circumference (level B) by the elastic compressive distal portion 14 must be an effective therapeutic pressure. The following values may be retained, depending on the patient's needs:

10 to 20 mmHg (13 to 27 hPa) for a relatively low compression of the ankle;
20 to 30 mmHg (27 to 40 hPa) for a moderate compression of the ankle.

The elastic compressive distal portion 14 that produces these therapeutic pressures is made from a knit fabric of more or less tight texture with incorporation of an elastic weft yarn, generally a covered spandex yarn, e.g. using:

as the weft yarn, a yarn such as spandex or a mixture of spandex and elasto-diene (synthetic rubber latex), covered with polyamide and/or cotton; and
as the knit yarn (stitch yarn), also a polyimide and/or cotton covered spandex yarn, having preferably a lower size (weight per unit length) than the weft yarn.

Characteristically of the invention, the proximal portion 16 is a splint portion (i.e. a portion that is essentially non-elastic in the final state of the orthosis), of tubular shape, extending:

in the vertical direction: over the extent of the calf, i.e. over the region comprised between the level B1 (junction between the Achilles tendon and the calf muscles) and the level D (below the knee), or at least over the major part of this region; it should be observed that the ankle (region extending around the level B) never belongs to this region covered by the proximal portion 16; and
in the circumference direction; over the whole circumference of the calf.

This non-elastic portion is made to measure, in the manner explained hereinafter, i.e. it has an external configuration that is accurately fitted to the shape and dimensions of the patients calf. As a result, once the orthosis slipped on the limb, this portion exerts the wanted splint effect, i.e., at rest, it exerts essentially no splinting force but, on effort, it opposes to the limb a rigidity providing the splint effect at the desired degree of effectiveness.

As regards the rigidity $R_c$ of this splint proximal portion 16, the following values may be retained (according to the above-mentioned European Pre-Standard XP ENV 12718: 2001):

for a strong splinting:
$R_c$=15±2 mmHg/cm (≈20±2 hPa/cm)
for a moderate splinting:
$R_c$=5 mmHg/cm (≈7 hPa/cm).

These values for $R_c$ are measured at the altitude C, i.e. at the point of maximum circumference of the calf.

By acting separately, on the one hand, on the elasticity of the compressive distal portion 14 at the ankle, and on the other hand, on the rigidity of the splint proximal portion 16 at the calf, it is possible to combine several compression/splinting effects, for example:

low compression at the ankle/high splint at the calf;
moderate compression at the ankle/high splint at the calf;
low compression at the ankle moderate splint at the calf; or
moderate compression at the ankle moderate splint at the calf.

Very advantageously, the distal portion 14 and the proximal portion 16 are both knitted continuously during a single sequence on the knitting machine, which avoids any step of making for assembling added parts. The proximal portion 16 may thus be knitted with the same types of yarns than the elastic compressive distal portion 14, i.e.:

as the weft yarn, a polyamide and/or cotton covered spandex yarn; and
as the knit yarn, a polyamide and/or cotton covered spandex yarn of lower size.

The product may be knitted according to usual techniques, on a conventional circular knitting machine, such as a Santoni knitting machine.

Characteristically of the invention, the non-elastic splint proximal portion 16 is obtained by adding a resin.

This operation is made as illustrated in FIG. 3.

The orthosis 10 that has just been knitted in the conventional manner is initially in the form of a standard product, i.e. a product that is not tailored to measure (step a); it is only provided, as for the conventional EVC orthoses, and even for any cloth article, suitable standard sizes, to be selected in a size grid.

This orthosis is then placed (step b) on a template 22 corresponding to the patient's morphology in the calf region.

This region may in particular be delimited by marks such as the marks 24, visible by transparency once the orthosis is slipped on.

The following step (step c) consists in adding in the calf region, i.e. between the marks 24, a biocompatible resin, for example by application with a brush 26, by controlled spraying or by dipping.

An example of resin that can be used for that purpose is, for example, the resin Plastidurex, which is a single-component acrylic resin sold by REAL Composites, and which is used, for example, in the field of decoration for the rigidification of papers and fabrics, the creation of lampshades, etc.

Another resin that can be used is the resin SILDOC RTV AD 35, which is a two-component silicone resin, also sold by REAL Composites, and which is used, for example, in the field of body molding.

This resin is applied until saturation of the textile, and is left to dry, by evaporation.

In an exemplary implementation, it has been observed that, after hardening by evaporation, 12 g of resin were added to the sock with respect to the initial weight of the latter, for an application in the calf region as defined hereinabove, over the whole circumference of the sock. The final rigidity obtained was about 15 mmHg/cm (20 mPa/cm).

The orthosis may then be removed from the template (step d). It will then have its definitive shape, "tailored to measure", with a splint proximal portion 16 that has become rigid and that has taken a shape that perfectly fits the curve and the dimensions of the patient's calf, and an elastic compressive distal part 14, which results in a product associating a high rigidity at the calf (splint proximal portion 16) and a low rigidity at the ankle (elastic compressive distal portion 14), providing a therapeutic-level compression of the lower limb.

The invention claimed is:

1. A method for tailoring an orthosis for medical compression/splinting of a lower limb to a measure of a patient's leg, said method comprising the steps of:
   obtaining an orthosis (10), said orthosis comprising:
   (i) an elastic compressive distal portion, adapted to cover an ankle, extending to before a beginning of a calf, at a point where an Achilles tendon joins calf muscles, the distal portion being made by knitting a knit yarn and a weft yarn, a dimensioning and a nature of the knit and weft yarns as well as a knit structure being selected in such a way to exert in a circumference direction, once that orthosis has been placed on the limb, an elastic return force likely to produce a compression of the limb at a desired therapeutic level of pressure, and
   (ii) a splint proximal portion, continuing the compressive distal portion and adjacent thereto, and enveloping, over a circumference thereof, a region of the calf comprised between a level of a point where the Achilles tendon joins the calf muscles and the level located below the tibial tuberosity;
   obtaining a hardenable biocompatible resin;
   placing the orthosis onto the patient's leg or a template representative of a morphology of the patient's calf;
   applying in situ on the orthosis over a whole circumference of a region of the splint proximal portion, said hardenable biocompatible resin;
   hardening the resin with the orthosis maintained on the patient's leg or the template; and
   removing the orthosis in a finished state, wherein the orthosis in the finished state is such that the splint proximal portion (16) is made rigid following the hardening of the resin and keeps corresponding dimensions of the patient's calf, which allows this splint proximal portion to perfectly fit a shape of the calf, while the compressive distal portion is still elastic to provide a therapeutic-level compression.

2. The method of claim 1, wherein the biocompatible resin is an evaporation-hardenable single component acrylic resin.

3. The method of claim 1, wherein the knit yarn and/or the weft yarn is a polyamide and/or cotton covered spandex yarn.

4. The method claim 1, wherein the splint proximal portion is a portion having, at a level of a calf maximum circumference, a high rigidity, of 15±2 mmHg/cm (≈20±2 mPa/cm).

5. The method of claim 1, wherein the splint proximal portion is a portion having, at a level of a calf maximum circumference, a moderate rigidity, of 5±2 mmHg/cm (≈7±2 mPa/cm).

6. The method of claim 1, wherein the elastic compressive distal portion is a low compression portion adapted to exert a pressure of 10 to 20 mmHg (13 to 27 hPa) at a level of an ankle minimum circumference.

7. The method of claim 1, wherein the elastic compressive distal portion is a moderate compression portion adapted to exert a pressure of 20 to 30 mmHg (27 to 40 hPa) at a level of an ankle minimum circumference.

8. The method of claim 1, wherein the biocompatible resin is applied with a brush, by controlled spraying or by dipping.

9. The method of claim 1, wherein in the finished state, the orthosis can be temporarily removed once it has been placed on said leg.

10. A kit to achieve a method according to claim 1, for tailoring an orthosis for medical compression/splinting of a leg of a patient, said leg comprising an ankle, an Achilles tendon, a tibial tuberosity, and a calf comprising calf muscles, said kit comprising:
    an orthosis comprising:
      an elastic compressive distal portion, adapted to cover said ankle, extending to before a beginning of said calf, at a point where the Achilles tendon joins said calf muscles, the elastic compressive distal portion being made by knitting a knit yarn and a weft yarn, a dimensioning and a nature of the knit and weft yarns as well as a knit structure being selected in such a way to exert in a circumference direction, once the orthosis has been placed on said leg, an elastic return likely to produce a compression of the leg at a desired therapeutic level of pressure, and
      a splint proximal portion, continuing the compression distal portion and adjacent thereto, and enveloping, over a circumference thereof, a region of the calf comprised between a level of the point where the Achilles tendon joins the calf muscles and a level located below the tibial tuberosity, and
    a hardenable biocompatible resin, separated from the orthosis.

11. A kit according to claim 10, wherein the elastic compressive distal portion and the splint proximal portion are both knitted continuously during a single sequence on a knitting machine.

12. A method to improve calf musculo-sponeurotic pump efficiency of a patient, wherein an orthosis manufactured according to claim 1 is placed on a leg of the patient.

* * * * *